(12) United States Patent
El A'mma

(10) Patent No.: US 6,403,533 B2
(45) Date of Patent: Jun. 11, 2002

(54) STABILIZED MICROBICIDE FORMULATION

(75) Inventor: Beverly Jean El A'mma, Perkiomenville, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/759,098

(22) Filed: Jan. 12, 2001

Related U.S. Application Data

(60) Provisional application No. 60/178,418, filed on Jan. 27, 2000.

(51) Int. Cl.$^7$ .......................... A01N 25/22; A01N 43/80
(52) U.S. Cl. ..................... 504/156; 514/372; 514/970
(58) Field of Search ..................... 504/156; 514/372; 106/15.05

(56) References Cited

U.S. PATENT DOCUMENTS

| | | | |
|---|---|---|---|
| 5,127,934 A | * 7/1992 | Mattox | 71/67 |
| 5,160,527 A | 11/1992 | Law et al. | 71/67 |
| RE34,185 E | 2/1993 | Amick | 548/213 |
| 5,461,150 A | 10/1995 | Gironda et al. | 548/213 |
| 5,559,083 A | * 9/1996 | Kubota et al. | 504/269 |
| 5,670,529 A | 9/1997 | Clarke | 514/360 |
| 5,910,503 A | 6/1999 | Mattox et al. | 514/372 |
| 5,955,486 A | 9/1999 | Mattox | 514/372 |
| 6,008,238 A | 12/1999 | El A'mma et al. | 514/372 |
| 6,211,213 B1 | 4/2001 | El A'mma | 514/372 |

FOREIGN PATENT DOCUMENTS

| | | |
|---|---|---|
| EP | 749689 A | 12/1996 |
| EP | 864406 A | 9/1998 |
| EP | 1044609 A | 10/2000 |
| JP | 2304005 | 12/1990 |

* cited by examiner

*Primary Examiner*—S. Mark Clardy
(74) *Attorney, Agent, or Firm*—Thomas J. Howell

(57) ABSTRACT

A method for stabilizing dilute solutions of 3-isothiazolone compounds against the formation of unwanted brown precipitate in the presence of low levels of copper, by the addition of 2 to 50% of selected water-soluble organic solvents, is disclosed. The aqueous solutions are substantially free of metal nitrate, metal nitrite and magnesium salt stabilizers.

13 Claims, No Drawings

STABILIZED MICROBICIDE FORMULATION

This application claims priorty from Provisional application Ser. No. 60/178,418, filed Jan. 27, 2000.

BACKGROUND

This invention relates to the stabilization of aqueous solutions of microbicides. In particular, this invention relates to the improved stabilization of dilute aqueous solutions of 3-isothiazolone compounds that contain low levels of cupric ion; preferably, the solutions are substantially free of metal salt stabilizers, such as nitrate, nitrite and magnesium salts.

Microbicides are used commercially to prevent the growth of microbes in a variety of loci, such as cooling towers, metal working fluid systems, paints and cosmetics. One of the more important classes of microbicides is 3-isothiazolones, which have achieved commercial success because they are very effective in preventing microbial growth under a wide variety of conditions and in a variety of loci. Among the most important 3-isothiazolones are 5-chloro-2-methyl-3-isothiazolone (CMI), 2-methyl-3-isothiazolone (MI) and mixtures thereof; particularly successful is a mixture of CMI and MI in an approximate ratio of 3:1.

While 3-isothiazolones are very effective microbicides, they suffer from being unstable under certain conditions. Without the presence of a stabilizer, many 3-isothiazolones chemically degrade and lose microbicidal efficacy and much research has been devoted to stabilizing 3-isothiazolones in various types of solutions, for example:

(1) "concentrates" contain 5 to 35%, typically 14 to 25%, by weight of CMI/MI;

(2) "dilute solutions" contain about 0.5 to 5% by weight of CMI/MI and are designed to be further diluted when added to a locus; and (3) "use dilution" solutions represent the end use dilution in the locus to be protected and contain substantially less than 1% by weight of CMI/MI. Concentrates and dilute solutions are sold commercially and are diluted and incorporated into loci as use dilutions. Each of these solutions presents special challenges to the stabilization of CMI and MI.

In general, compounds that stabilize 3-isothiazolone concentrates do not stabilize 3-isothiazolone dilute solutions. Compounds, such as magnesium nitrate, that do stabilize both 3-isothiazolone concentrates and dilute solutions do so in greatly differing amounts. More magnesium nitrate is required to stabilize a 3-isothiazolone dilute solution than a concentrate; for example, 23% is used for dilute solutions as compared to 10 to 25%, preferably 12 to 16%, for concentrates. Dilute solutions containing 1.5% CMI/MI are typically stabilized either with high levels of magnesium nitrate (23%), or with a combination of low levels of magnesium nitrate (1.5–5%) and low levels of copper nitrate (0.037–0.14% as copper ion), or with a combination of low levels of magnesium nitrate (1.5–5%) and 0.6% hydrogen peroxide. Dilute solutions containing 4% CMI/MI are typically stabilized with a combination of 4.6% magnesium nitrate and 4% copper sulfate.

These known stabilized 3-isothiazolone dilute solutions suffer from having a high metal salt content or having limited stability. When a 3-isothiazolone stabilized with a metal salt is added to a latex formulation, the high metal salt content can coagulate the latex. There is also concern regarding nitrates in certain applications where amines may be present because of the possibility of nitrosamine formation. As little as 0.14% copper nitrate is a concern in some countries due to limits on the amount of copper permitted in water discharge streams.

Although the above described stabilizers for 3-isothiazolone dilute solutions allow the 3-isothiazolones to retain their microbicidal efficacy for considerable periods of time, they do not prevent other problems from developing, such as the formation of brown precipitate upon storage. The presence of this brown precipitate does not impact the efficacy of the 3-isothiazolones; however, the presence of the brown precipitate gives an undesirable appearance to users of the product. It is clearly preferable from a commercial standpoint to have a product which does not form a brown precipitate.

U.S. Pat. No. Re. 34,185 discloses that non-aqueous solutions of 3-isothiazolones can be stabilized against chemical decomposition by using organic hydroxylic solvents, such as ethylene glycol.

U.S. Pat. No. 5,461,150 discloses the stabilization of aqueous solutions of 3-isothiazolones with a low level of cupric ion. While these latter compositions are chemically stable, they suffer from the formation of a brown precipitate upon storage. Such brown precipitate is particularly undesirable when the compositions are used to preserve cosmetics and toiletries.

U.S. Pat. Nos. 5,955,486 and U.S. Pat. No. 5,910,503 disclose methods to prevent the formation of precipitate in 3-isothiazolone concentrates by the addition of chlorate, perchlorate, nitrate and iodate salts; these formulations involve the use of relatively high levels of inorganic metal salt stabilizers. U.S. Pat. No. 6,008,238 discloses the use of inorganic oxidant salts to prevent the formation of precipitate in dilute aqueous solutions of 3-isothiazolones.

The problem addressed by the present invention is to overcome the formation of brown precipitate that occurs in 3-isothiazolone dilute solution compositions that are otherwise chemically stable, while maintaining an overall low inorganic metal salt content.

SUMMARY OF INVENTION

The present invention provides a microbicide composition comprising (a) 0.5 to 5 percent, based on the weight of the composition, of a water-soluble 3-isothiazolone; (b) 2 to 50 percent, based on the weight of the composition, of a water-soluble organic solvent selected from one or more of polyols having molecular weights up to 200; $(C_1-C_4)$alkyl esters of acetic acid and propionic acid; and $(C_2-C_4)$ alcohols; (c) 0.0005 to 0.1 percent, based on the weight of the composition, of a cupric ion in the form of a copper salt; and (d) water; wherein the composition is free of brown precipitate for at least 4 weeks when maintained at a temperature of 55° C.

A preferred embodiment of the present invention provides the aforementioned composition wherein the composition is substantially free of metal nitrite, metal nitrate and magnesium salts.

In another embodiment the present invention provides a method of stabilizing a microbicide composition against the formation of brown precipitate comprising combining (a) 2 to 50 percent, based on the weight of the composition, of a water-soluble organic solvent selected from one or more of polyols having molecular weights up to 200; $(C_1-C_4)$alkyl esters of acetic acid and propionic acid; and $(C_2-C_4)$ alcohols; (b) 0.0005 to 0.1 percent, based on the weight of the composition, of a cupric ion in the form of a copper salt; (c) 0.5 to 5 percent, based on the weight of the composition, of a water-soluble 3-isothiazolone; and (d) water.

The present invention also provides a method of controlling or inhibiting the growth of microorganisms in a locus comprising introducing to the locus a composition as described above.

DETAILED DESCRIPTION

We have discovered that 3-isothiazolone dilute aqueous solution compositions containing from 5 to 1000 ppm (0.0005 to 0.1%) copper ion can be effectively stabilized against the formation of brown precipitates by incorporating specific concentrations of selected water-soluble organic solvents into the composition. Preferably the solutions are substantially free of metal nitrate, metal nitrite or magnesium salt stabilizers; these "nitrate-free" extremely low level copper-stabilized and organic-solvent stabilized aqueous compositions are especially useful to protect cosmetic compositions.

Preferably the compositions of the present invention also have a low total inorganic metal salt content, that is, they typically contain zero or up to 0.5%, preferably zero or less than 0.2%, more preferably zero or up to 0.15% and most preferably zero or up to 0.1%, of total inorganic metal salts, based on weight of the composition.

As used herein, the following terms have the designated definitions, unless the context clearly indicates otherwise. The term "microbicide" refers to a compound capable of inhibiting the growth of or controlling the growth of microorganisms at a locus; microbicides include bactericides, fungicides and algaecides. The term "microorganism" includes, for example, fungi, bacteria and algae. The term "locus" refers to an industrial system or product subject to contamination by microorganisms. "Nitrate-free" or "substantially free of metal nitrate, metal nitrite and magnesium salts" means that the aqueous composition contains zero or less than 0.1%, preferably zero or up to 0.05%, and more preferably zero or up to 0.01%, of metal nitrate or metal nitrite salt, based on weight of the composition; and for magnesium salts it means that the aqueous composition contains zero or up to 0.5%, preferably zero or up to 0.1%, and more preferably zero or up to 0.05%, of magnesium salt, based on weight of the composition.

The following abbreviations are used throughout the specification: HPLC=high performance liquid chromatography; ppm=parts per million by weight (weight/weight); g=gram; ml=milliliter. Unless otherwise specified, ranges listed are to be read as inclusive and combinable, temperatures are in degrees centigrade (° C.), and references to percentages (%) are by weight.

Any water-soluble 3-isothiazolone compound is useful in the compositions of the present invention. Water-soluble 3-isothiazolone compounds are those having a water solubility greater than 1000 ppm. Suitable 3-isothiazolone compounds include, for example: 5-chloro-2-methyl-3-isothiazolone (CMI), 2-methyl-3-isothiazolone (MI), 2-ethyl-3-isothiazolone, 5-chloro-2-ethyl-3-isothiazolone and 4,5-dichloro-2-methyl-3-isothiazolone. Preferred 3-isothiazolones are 5-chloro-2-methyl-3-isothiazolone and 2-methyl-3-isothiazolone, either alone or in admixture. When mixtures of 5-chloro-2-methyl-3-isothiazolone and 2-methyl-3-isothiazolone are used, the weight ratio of 5-chloro-2-methyl-3-isothiazolone to 2-methyl-3-isothiazolone is generally from 99:1 to 0.5:99.5, preferably from 90:10 to 2:98 and more preferably from 75:25 to 80:20.

The amount of water-soluble 3-isothiazolone compound useful in the compositions of the present invention is 0.5 to 5%, preferably from 0.5 to 4%, more preferably from 1 to 3%, and most preferably from 1 to 2%, based on weight of the composition.

Water-soluble organic solvents useful in the present invention, include, for example: polyols having molecular weights up to 200 (for example, alkyleneoxide glycols such as ethylene glycol, diethylene glycol, polyethylene glycols, propylene glycol, dipropylene glycol and polypropylene glycols; alkanediols such as 1,3-butanediol, 1,4-pentanediol and 1,5-pentanediol; and alkanetriols such as glycerol); ($C_1$-$C_4$)alkyl esters of acetic acid and propionic acid (for example, methyl acetate, ethyl acetate, ethyl propionate and butyl acetate); and ($C_2$-$C_4$) alcohols (for example, ethanol, n-propanol, isopropanol, n-butanol, isobutyl alcohol, sec-butyl alcohol and tert-butyl alcohol). Preferably the water-soluble organic solvent is selected from one or more of propylene glycol, dipropylene glycol and 1,3-butanediol.

The amount of water-soluble organic solvent useful in the compositions of the present invention is from 2 to 50%, preferably from 2 to 40%, more preferably from 5 to 20% and most preferably from 5 to 15%, based on weight of the composition. At levels of water-soluble organic solvent below 2%, prevention of the brown precipitate formation is not satisfactory. At levels of water-soluble organic solvent above 50%, homogeneity and compatibility of components in the aqueous composition may be affected, for example, undesirable viscosity increases or phase separations; in addition, it is desirable to minimize the concentration of organic solvent in the compositions due to recent regulations on VOC (volatile organic compound) concentrations, while at same time using sufficient organic solvent to provide protection against the formation of brown precipitate on storage.

A wide variety of copper salts are known in the art. Any copper salt which is sufficiently water soluble to provide the desired level of cupric ion in solution may be used in the compositions of the present invention. Suitable copper salts include, for example: copper sulfate, copper acetate, copper chloride, copper bromide, copper iodide, copper chlorate, copper perchlorate and copper gluconate; copper sulfate and copper chlorate are preferred salts. The copper salts are generally commercially available, for example, from Pfalz and Bauer (Waterbury, Conn.), and may be used without further purification. Mixtures of copper salts may also be used.

The amount of copper ion useful in the compositions of the present invention is from 0.0005 to 0.1%, preferably from 0.001 to 0.05% and more preferably from 0.001 to 0.02%, corresponding to 5 to 1000 ppm, 10 to 500 ppm and 10 to 200 ppm, respectively. Typically, the copper ion and 3-isothiazolone are present in a ratio of 1/10,000 to 1/5, preferably from 1/2,000 to 1/50, more preferably from 1/1,000 to 1/100 and most preferably from 1/500 to 1/100.

Particularly useful compositions of the present invention include, for example, 1 to 2% of a water-soluble 3-isothiazolone selected from one or more of 5-chloro-2-methyl-3-isothiazolone and 2-methyl-3-isothiazolone; 5 to 15% of a water-soluble organic solvent selected from one or more of propylene glycol, dipropylene glycol and 1,3-butanediol; 0.001 to 0.02% cupric ion in the form of a copper salt selected from one or more of copper sulfate and copper chlorate; and water. Preferably, the ratio of copper ion to 3-isothiazolone compound is from 1/500 to 1/100 and the composition is substantially free of metal nitrate, metal nitrite and magnesium salts.

In preparing the compositions of the present invention, the water-soluble organic solvent, the 3-isothiazolone, copper salt and water can be mixed in any order. The compositions of the present invention are preferably prepared by adding the 3-isothiazolone to a mixture of organic solvent, copper salt and water.

An advantage of the compositions of the present invention is that they are both physically and chemically stable as prepared and upon storage. That is, these dilute solutions of 3-isothiazolone remain physically stable upon storage and do not settle or separate into different phases. By "physically stable" we mean that the compositions are fluid and show no visible brown precipitate formation after storage for at least 4 weeks at 55° C., and preferably for at least 8 weeks at 55° C. By "chemically stable" is meant that the 3-isothiazolone, particularly the CMI compound, retains at least 60%, preferably at least 70% and more preferably at least 80%, of its original concentration in the dilute solution composition after storage for at least 4 weeks at 55° C., and preferably for at least 8 weeks at 55° C.

Dilute solutions prepared according to the present invention do not require additional stabilizer, thus reducing the cost and extra handling associated with the use of known 3-isothiazolone concentrates. One of the further advantages of the present invention is that the 3-isothiazolone dilute solutions do not cause coagulation when added to latexes.

The compositions of the present invention can be used to inhibit the growth of microorganisms by introducing a microbicidally effective amount of the compositions onto, into, or at a locus subject to microbial attack. Suitable loci include, for example: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions; dispersions; paints; latexes; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom disinfectants or sanitizers; cosmetics; toiletries; shampoos; soaps; detergents; industrial disinfectants or sanitizers, such as cold sterilants, hard surface disinfectants; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; pools; and spas.

Preferably, the compositions of the present invention are used to inhibit the growth of microorganisms at a locus selected from one or more of emulsions, dispersions, paints, latexes, household products, cosmetics, toiletries, shampoos, soaps, detergents, industrial disinfectants and industrial sanitizers.

The amount of 3-isothiazolone compounds suitable to inhibit or control the growth of microorganisms is well known in the art and depends upon the locus to be protected. The amount of 3-isothiazolone microbicide suitable to inhibit the growth of microorganisms is generally between 0.05 and 5,000 ppm, and preferably between 0.1 and 2,500 ppm, based on the locus to be protected. For example, loci such as a cooling tower or pulp and paper processing fluids require 0.1 to 100 ppm, and preferably 0.1 and 50 ppm, of the 3-isothiazolone microbicides to inhibit microorganism growth. Other loci, such as construction products, oilfield fluids or emulsions, require 0.5 to 5,000 ppm of the 3-isothiazolone microbicides to inhibit microorganism growth, while loci such as disinfectants or sanitizers may require up to 5,000 ppm; cosmetic formulations typically require from 1 to 500 ppm.

It is known in the art that the performance of antimicrobial agents may be enhanced by combination with one or more other antimicrobial agents. Thus, other known microbicidal agents may be combined advantageously with the compositions of the present invention.

Some embodiments of the invention are described in detail in the following Examples. All ratios, parts and percentages are expressed by weight unless otherwise specified, and all reagents used are of good commercial quality unless otherwise specified. The level of copper is reported in ppm as the level of cupric ion. Samples were considered stable when the samples were free of brown precipitate after being stored at least 4 weeks, and preferably at least 8 weeks, at 55° C. Abbreviations used in the Examples and Tables are listed below with the corresponding descriptions.

| | |
|---|---|
| CMI = | 5-Chloro-2-methyl-3-isothiazolone |
| MI = | 2-Methyl-3-isothiazolone |
| PG = | Propylene Glycol (1,2-Propanediol) |
| DPG = | Dipropylene Glycol |
| 1,5-PD = | 1,5-Pentandiol (Pentamethylene Glycol) |
| 1,3-BD = | 1,3-Butanediol (1,3-Butylene Glycol) |
| PPG-425 = | Polypropylene Glycol (MW = 425) |
| EtOH = | Ethanol |
| EtOAc = | Ethyl Acetate |
| MW = | Molecular Weight |
| DI = | Deionized |

EXAMPLE 1

The samples tested were prepared by adding known amounts of 3-isothiazolone, copper sulfate pentahydrate, water-soluble organic solvent and DI water to a 100-ml glass jar equipped with a magnetic stir bar. The 3-isothiazolone used was an approximate 3:1 (weight/weight) mixture of CMI and MI (98% purity). Ingredients were combined in a manner to provide test solutions containing 1.5% of the 3-isothiazolone (1.53 g per 100 g total solution), 30 ppm copper ion (0.0118 g copper sulfate pentahydrate per 100 g total solution) and various concentrations of water-soluble organic solvent (0 g, 1 g, 5 g, 10 g, 25 g and 50 g per 100 g total solution, corresponding to 0%, 1%, 5%, 10%, 25% or 50% solvent, respectively); the remainder of the solution (to 100 g total) was made up with DI water. Each sample was stirred until all solids were dissolved; portions (approximately 10 g) were then transferred to 20-ml glass vials and stored at room temperature or in an oven at 55° C. The samples were visually examined at various time points to determine the formation of brown precipitate and analyzed by HPLC/UV detection to determine the amount of CMI remaining; in all cases the amount of remaining MI was unchanged (100% of original value).

EXAMPLE 2

Tables 1 and 1A summarize the stabilizing effect of various water-soluble organic solvents on aqueous solutions of CMI/MI regarding the prevention of brown precipitate formation upon storage at 55° C. Table 1 shows that, although propylene glycol (PG) is an effective stabilizing solvent above levels of 1%, the use of polypropylene glycol (PPG-425) having a molecular weight of 425 (approximately 6 monomeric repeat units) is ineffective (brown precipitate formation or phase separation) at all use levels from 1 to 50%.

TABLE 1

| Solvent | Weeks of Storage | Temperature (° C.) | Brown Precipitate Formation | % CMI Remaining |
|---|---|---|---|---|
| None | 0 | 25 | No | 100 |
|  | 4 | 55 | No | 88 |
|  | 8 | 55 | Yes | 59 |
| PG (1%) | 0 | 25 | No | 100 |
|  | 4 | 55 | Yes | 88 |
|  | 8 | 55 | Yes | 59 |
| PG (5%) | 0 | 25 | No | 100 |
|  | 4 | 55 | No | 94 |
|  | 8 | 55 | No | 73 |
| PG (10%) | 0 | 25 | No | 100 |
|  | 4 | 55 | No | 93 |
|  | 8 | 55 | No | 66 |
| PG (25%) | 0 | 25 | No | 100 |
|  | 4 | 55 | No | 95 |
|  | 8 | 55 | No | 80 |
| PG (50%) | 0 | 25 | No | 100 |
|  | 4 | 55 | No | 99 |
|  | 8 | 55 | No | 73 |
| PPG-425 (1%) | 0 | 25 | No | 100 |
|  | 4 | 55 | Yes | 94 |
|  | 8 | 55 | Yes | 53 |
| PPG-425 (5%) | 0 | 25 | No | 100 |
|  | 4 | 55 | No | 94 |
|  | 8 | 55 | Yes | 54 |
| PPG-425 (10%) | 0 | 25 | No | 100 |
|  | 4 | 55 | Yes | 92 |
|  | 8 | 55 | Yes | 27 |
| PPG-425 (25%) | 0 | 25 | No | 100 |
|  | 4 | 55 | Yes* | 98 |
|  | 8 | 55 | Yes* | 0 |
| PPG-425 (50%) | 0 | 25 | No | 100 |
|  | 4 | 55 | Yes* | 98 |
|  | 8 | 55 | Yes* | 0 |

*= phase separation

Table 1A shows that 1,5-pentanediol, ethanol and ethyl acetate are also effective stabilizing solvents at use levels above 1%, using the same source (lot) of 3-isothiazolone (CMI/MI mixture) as was used in Table 1 experiments.

TABLE 1A

| Solvent | Weeks of Storage | Temperature (° C.) | Brown Precipitate Formation | % CMI Remaining |
|---|---|---|---|---|
| 1,5-PD (1%) | 0 | 25 | No | 100 |
|  | 4 | 55 | No | 88 |
|  | 8 | 55 | Yes | 67 |
| 1,5-PD (5%) | 4 | 55 | No | 97 |
|  | 8 | 55 | No | 88 |
| 1,5-PD (10%) | 4 | 55 | No | 97 |
|  | 8 | 55 | No | 90 |
| 1,5-PD (25%) | 4 | 55 | No | 99 |
|  | 8 | 55 | No | 98 |
| 1,5-PD (50%) | 4 | 55 | No | 100 |
|  | 8 | 55 | No | 98 |
| EtOH (10%) | 4 | 55 | No | 98 |
|  | 8 | 55 | No | 82 |
| EtOAc (10%) | 4 | 55 | No | 90 |
|  | 8 | 55 | No | 79 |

EXAMPLE 3

Table 2 summarizes the stabilizing effect of additional water-soluble organic solvents on aqueous solutions of CMI/MI regarding the prevention of brown precipitate formation upon storage at 55° C., using a different source (lot) of CMI/MI mixture from that used in Example 2.

TABLE 2

| Solvent | Weeks of Storage | Temperature (° C.) | Brown Precipitate Formation | % CMI Remaining |
|---|---|---|---|---|
| None | 0 | 25 | No | 100 |
|  | 4 | 55 | Yes | 86 |
|  | 8 | 55 | Yes | 68 |
| 1,3-BG (10%) | 4 | 55 | No | 96 |
|  | 8 | 55 | No | 95 |
| 1,3-BG (25%) | 4 | 55 | No | 99 |
|  | 8 | 55 | No | 100 |
| 1,3-BG (50%) | 4 | 55 | No | 99 |
|  | 8 | 55 | No | 100 |
| DPG (10%) | 4 | 55 | No | 98 |
|  | 8 | 55 | No | 96 |
| DPG (20%) | 4 | 55 | No | 99 |
|  | 8 | 55 | No | 100 |
| DPG (50%) | 4 | 55 | No | 99 |
|  | 8 | 55 | No | 100 |
| PG (10%) | 4 | 55 | No | 100 |
|  | 8 | 55 | No | 98 |
| PG (25%) | 4 | 55 | No | 99 |
|  | 8 | 55 | No | 99 |
| PG (50%) | 4 | 55 | No | 99 |
|  | 8 | 55 | No | 100 |

EXAMPLE 4

Table 3 effect of different levels of copper ion using 3 different sources (lots) of 3-isothiazolone (CMI/MI mixture) in the presence of 10% propylene glycol solvent. The presence of both copper ion and the water-soluble solvent is required to provide the desired combination of (i) isothiazolone chemical stability (note that the CMI component has totally degraded in the absence of copper) and (ii) absence of brown precipitate upon storage. The range of levels for "%CMI remaining" in the table is representative of the 3 different lots of 3-isothiazolone used in the study.

TABLE 3

| Copper Ion (ppm) | Weeks of Storage | Temperature (° C.) | Brown Precipitate Formation | % CMI Remaining |
|---|---|---|---|---|
| None | 0 | 25 | No | 100/100/100 |
|  | 4 | 55 | No | 0/0/0 |
|  | 8 | 55 | No | 0/0/0 |
| 30 | 4 | 55 | No | 98/96/98 |
|  | 8 | 55 | No | 95/100/100 |
| 100 | 4 | 55 | No | 96/98/98 |
|  | 8 | 55 | No | 99/100/100 |

What is claimed is:

1. A microbicide composition comprising:
 (a) 0.5 to 5 percent, based on the weight of the composition, of a water-soluble 3-isothiazolone;
 (b) 2 to 50 percent, based on the weight of the composition, of a water-soluble organic solvent selected from one or more of polyols having molecular weights up to 200; ($C_1$-$C_4$)alkyl esters of acetic acid and propionic acid; and ($C_2$-$C_4$) alcohols;
 (c) 0.0005 to 0.1 percent, based on the weight of the composition, of a cupric ion in the form of a copper salt; and
 (d) water;
wherein the composition is free of brown precipitate for at least 4 weeks when maintained at a temperature of 55° C. and the composition is substantially free of metal nitrite, metal nitrate and magnesium salts.

2. The composition of claim 1 where the 3-isothiazolone is selected from one or more of 5-chloro2-methyl-3isothiazolone, 2-methyl3isothiazolone, 2-ethyl3-isothiazolone, 5-chloro-2ethyl-3-isothiazolone and 4,5-dichloro-2-methyl-3-isothiazolone.

3. The composition of claim 2 wherein the 3-isothiazolone is selected from one or more of 5-chloro-2-methyl-3-isothiazolone and 2-methyl-3-isothiazolone.

4. The composition of claim 1 wherein the water-soluble organic solvent is selected from one or more of ethylene glycol, diethylene glycol, polyethylene glycols, propylene glycol, dipropylene glycol, polypropylene glycols, 1,3-butanediol, 1,4-pentanediol, 1,5-pentanediol, glycerol, methyl acetate, ethyl acetate, ethyl propionate, butyl acetate, ethanol, n-propanol, isopropanol, n-butanol, isobutyl alcohol, sec-butyl alcohol and tert-butyl alcohol.

5. The composition of claim 4 wherein the water-soluble organic solvent is selected from one or more of propylene glycol, dipropylene glycol and 1,3-butanediol.

6. The composition of claim 1 wherein the copper salt is selected from one or more of copper sulfate, copper acetate, copper chloride, copper bromide, copper iodide, copper chlorate, copper perchlorate and copper gluconate.

7. The composition of claim 1 comprising from 5 to 20 percent of water-soluble organic solvent.

8. The composition of claim 1 comprising from 0.001 to 0.05 percent of cupric ion.

9. The composition of claim 1 wherein the composition is free of brown precipitate for at least 8 weeks when maintained at a temperature of 55° C.

10. A microbicide composition comprising:
  (a) 1 to 2 percent, based on the weight of the composition, of a water-soluble 3-isothiazolone selected from one or more of 5-chloro-2-methyl-3-isothiazolone and 2-methyl-3-isothiazolone;
  (b) 5 to 15 percent, based on the weight of the composition, of a water-soluble organic solvent selected from one or more of propylene glycol, dipropylene glycol and 1,3-butanediol;
  (c) 0.001 to 0.02 percent, based on the weight of the composition, of a cupric ion in the form of a copper salt selected from one or more of copper sulfate and copper chlorate; and
  (d) water;
wherein the composition is free of brown precipitate for at least 4 weeks when maintained at a temperature of 55° C.; the ratio of copper ion to 3-isothiazolone compound is from 1/500 to 1/100; and the composition is substantially free of metal nitrate, metal nitrite and magnesium salts.

11. A method of controlling or inhibiting the growth of microorganisms in a locus comprising introducing to the locus the composition of claim 1.

12. The method of claim 11 wherein the locus is selected from one or more of emulsions, dispersions, paints, latexes, household products, cosmetics, toiletries, shampoos, soaps, detergents, industrial disinfectants and industrial sanitizers.

13. A method of stabilizing a microbicide composition against the formation of brown precipitate comprising combining:
  (a) 2 to 50 percent, based on the weight of the composition, of a water-soluble organic solvent selected from one or more of polyols having molecular weights up to 200; $(C_1$–$C_4)$alkyl esters of acetic acid and propionic acid; and $(C_2$–$C_4)$ alcohols;
  (b) 0.0005 to 0.1 percent, based on the weight of the composition, of a cupric ion in the form of a copper salt;
  (c) 0.5 to 5 percent, based on the weight of the composition, of a water-soluble 3-isothiazolone; and
  (d) water;
wherein the composition is substantially free of metal nitrite, metal nitrate and magnesium salts.

* * * * *